(12) United States Patent
Balestra et al.

(10) Patent No.: US 6,683,090 B1
(45) Date of Patent: Jan. 27, 2004

(54) N-AZABICYCLO-AMIDE DERIVATIVES

(75) Inventors: Michael Balestra, Wilmington, DE (US); George Mullen, Waltham, MA (US); Eifion Phillips, Wilmington, DE (US); Richard Schmiesing, Wilmington, DE (US)

(73) Assignee: Astrazeneca AB, Sodertalje (SE)

( * ) Notice: Subject to any disclaimer, the term of this patent is extended or adjusted under 35 U.S.C. 154(b) by 0 days.

(21) Appl. No.: 10/130,635

(22) PCT Filed: Nov. 16, 2000

(86) PCT No.: PCT/SE00/02262

§ 371 (c)(1),
(2), (4) Date: May 17, 2002

(87) PCT Pub. No.: WO01/36417

PCT Pub. Date: May 25, 2001

(30) Foreign Application Priority Data

Nov. 18, 1999 (SE) .................................. 9904176

(51) Int. Cl.$^7$ .................... C07D 543/02; A61K 31/439; A61K 31/40
(52) U.S. Cl. ................. 514/305; 514/305; 546/135
(58) Field of Search ............ 546/135; 514/305

(56) References Cited

U.S. PATENT DOCUMENTS 5,981,525 A * 11/1999 Farina et al. ............. 514/235.2

FOREIGN PATENT DOCUMENTS

| EP | 0581165 A2 | 2/1994 |
|----|------------|--------|
| EP | 0581165 | * 2/1994 |
| WO | WO 9420465 A1 | 9/1994 |

OTHER PUBLICATIONS

STN International, File CAPLUS, CAPLUS accession No. 1995:904880, Document No. 124:649, Kostochka, L.M. et al. "Synthesis and local–anesthetic activity of tropane enamides and amides"; Khim.–Farm. Zh. (1995), 29(3), 40–2.

* cited by examiner

Primary Examiner—Rita Desai
(74) Attorney, Agent, or Firm—Kenneth F. Mitchell

(57) ABSTRACT

Compounds of the general formula I

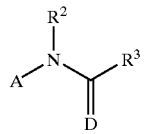

I wherein A represents:

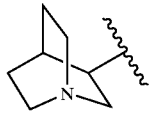

II

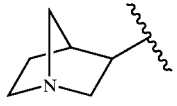

III

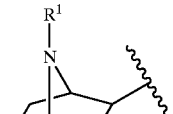

IV

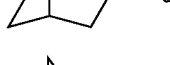

V

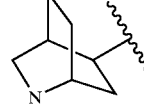

or

VI

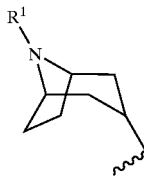

D represents oxygen, or sulfur and $R^1$, $R^2$ and $R^3$ are as defined in the specification, enantiomers thereof, pharmaceutically-acceptable salts thereof, processes for preparing them, pharmaceutical compositions containing them and their use in therapy, especially in the treatment or prophylaxis of psychotic disorders and intellectual impairment disorders.

10 Claims, No Drawings

N-AZABICYCLO-AMIDE DERIVATIVES

CROSS REFERENCE TO RELATED APPLICATIONS

This is a 371 filing of International Application No. PCT/SE00/02262 filed Nov. 16, 2000, pending, which claims priority under the Paris Convention of Application No. 9904176-6 filed in Sweden on Nov. 18, 1999.

TECHNICAL FIELD

This invention relates to new medical use of quinuclidine acrylamides or pharmaceutically acceptable salts thereof, processes for preparing them and pharmaceutical compositions containing them. The present invention also relates to certain novel quinuclidine acrylamides or pharmaceutically acceptable salts thereof, processes for preparing them and pharmaceutical compositions containing them. In particular the invention relates to the use of quinuclidine acrylamnides for the preparation of medicaments for the treatment or prophylaxis of psychotic disorders or intellectual impairment disorders, as well as in the treatment and/or prophylaxis of human diseases or conditions in which activation of the α7 nicotininc receptor is beneficial.

BACKGROUND OF THE INVENTION

The use of compounds which bind nicotinic acetylcholine receptors in the treatment of a range of disorders involving reduced cholinergic function such as Alzheimer's disease, cognitive or attention disorders, anxiety, depression, smoking cessation, neuroprotection, schizophrenia, analgesia, Tourette's syndrome, and Parkinson's disease has been discussed in McDonald et al. (1995) "Nicotinic Acetylcholine Receptors: Molecular Biology, Chemistry and Pharmacology", Chapter 5 in Annual Reports in Medicinal Chemistry, vol. 30, pp. 41–50, Academic Press Inc., San Diego, Calif.; and in Williams et al. (1994) "Neuronal Nicotinic Acetylcholine Receptors," Drug News & Perspectives, vol. 7, pp. 205–223.

The use of certain quinuclidine acrylamide derivatives, as to which the present invention has found a new pharmacological use, is known from EP 581165-A2 to have effect as antitussives. The antitussive activity of the compounds was described as being "without effects on the central nervous system", and the use of the compounds for the treatment of diseases involving the central nervous system was not suggested.

DISCLOSURE OF THE INVENTION

According to the present invention it has been found that compounds of the general formula I:

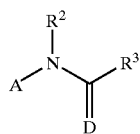

I wherein:
A represents:

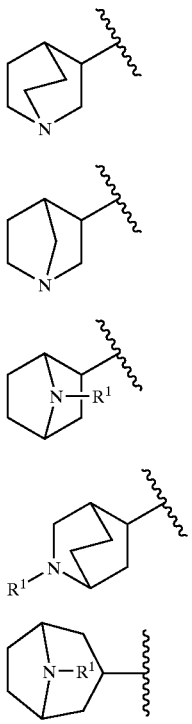

D represents oxygen, or sulfur;
$R^1$ represents hydrogen or methyl;
$R^2$ represents hydrogen, or $C_1$–$C_4$ alkyl;
$R^3$ represents:

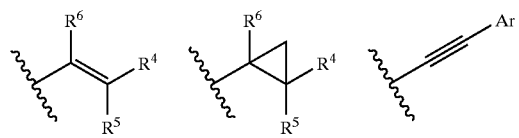

$R^4$, $R^5$, and $R^6$ are independently hydrogen, halogen, $C_1$–$C_4$ alkyl, $C_2$–$C_4$ alkenyl, $C_2$–$C_4$ alkynyl, —$CO_2R^7$, —CN, —$CF_3$, or Ar, provided that at least one of $R^4$ and $R^5$ represents Ar; Ar represents a 5- or 6-membered aromatic or heteroaromatic ring containing zero to three nitrogen atoms, zero or one oxygen atom, and zero or one sulfur atom, or an 8-, 9- or 10-membered fused aromatic or heteroaromatic ring system containing zero to four nitrogen atoms, zero to one oxygen atoms, and zero to one sulfur atoms which may optionally be substituted with one or more substituents selected from the following: hydrogen, halogen, $C_1$–$C_4$ alkyl, $C_2$–$C_4$ alkenyl, $C_2$–$C_4$ alkynyl, aryl, heteroaryl, —$CO_2R^7$, —CN, —$NO_2$, —$NR^8R^9$, —$CF_3$, —$OR^{10}$;
$R^8$, $R^9$, and $R^{10}$ are independently hydrogen, $C_1$–$C_4$ alkyl, aryl, heteroaryl, —$C(O)R^{11}$, —$C(O)NHR^{12}$, —$C(O)R^{13}$, —$SO_2R^{14}$ or $R^8$ and $R^9$ may together be $(CH_2)_jQ(CH_2)_k$ where Q is O, S, $NR^{15}$, or a bond;
j is 2 to 4;
k is 0 to 2;
$R^7$, $R^{10}$, $R^{11}$, $R^{12}$, $R^{13}$, $R^{14}$, and $R^{15}$, are independently $C_1$–$C_4$ alkyl, aryl, or heteroaryl;

or an enantiomer thereof, and pharmaceutically acceptable salts thereof, are useful for the preparation of a medicament for the treatment or prophylaxis of psychotic disorders or intellectual impairment disorders.

Examples of such conditions, diseases or disorders are Alzheimers disease, learning deficit, cognition deficit, attention deficit, memory loss, Attention Deficit Hyperactivity Disorder, anxiety, schizophrenia, mania or manic depression, Lewy Body Dementia, Parkinson's disease, Huntington's disease, Tourette's syndrome, neurodegenerative disorders in which there is loss of cholinergic synapse, jetlag, cessation of smoking, nicotinic addiction including that resulting from exposure to products containing nicotine, pain, and for ulcerative colitis.

Unless otherwise indicated, the $C_1$–$C_4$ alkyl groups referred to herein, e.g., methyl, ethyl, n-propyl, n-butyl, i-propyl, i-butyl, t-butyl, s-butyl, whether alone or part of another group, may be straight-chained or branched, and the $C_3$–$C_4$ alkyl groups may also be cyclic, e.g., cyclopropyl, cyclobutyl.

Unless otherwise indicated, aryl refers to a phenyl ring which may optionally be substituted with one to three of the following substituents chosen from among the following: halogen, $C_1$–$C_4$ alkyl, $C_2$–$C_4$ alkenyl, $C_2$–$_4$ alkynyl, —$CO_2R^7$, —CN, —$NO_2$, —$NR^8R^9$, —$CF_3$, —$OR^{10}$.

Unless otherwise indicated, heteroaryl refers to a 5- or 6-membered aromatic or heteroaromatic ring containing zero to three nitrogen atoms, zero or one oxygen atom, and zero or one sulfur atom, provided that the ring contains at least one nitrogen, oxygen, or sulfur atom, which may optionally be substituted with one or more substituents chosen from among the following: halogen, $C_1$–$C_4$ alkyl, $C_2$–$C_4$ alkenyl, $C_2$–$C_4$ alkynyl, —$CO_2R^7$, —CN, —$NO_2$, —$NR^8R^9$, $CF_3$, —$OR^{10}$.

Unless otherwise indicated, halogen refers to fluorine, chlorine, bromine, or iodine.

Pharmaceutically acceptable derivatives include solvates and salts. For example, the compounds of formula I can form acid addition salts with acids, such as the conventional pharmaceutically acceptable acids, for example, maleic, hydrochloric, hydrobromic, phosphoric, acetic, fumaric, salicylic, citric, lactic, mandelic, tartaric and methanesulfonic acids.

Preferred embodiments of the invention include compounds of formula I, wherein A represents:

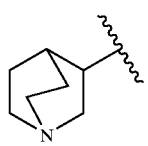

II or an enantiomer thereof, and pharmaceutically acceptable salts thereof.

Preferred embodiments of the invention also include compounds of formula I, wherein D represents oxygen; or an enantiomer thereof, and pharmaceutically acceptable salts thereof.

Preferred embodiments of the invention also include compounds of formula I, wherein $R^2$ represents hydrogen; or an enantiomer thereof, and pharmaceutically acceptable salts thereof.

Preferred embodiments of the invention also include compounds of formula I, wherein $R^3$ represents:

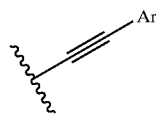

or an enantiomer thereof, and pharmaceutically acceptable salts thereof.

Preferred embodiments of the invention also include compounds of formula I, wherein $R^3$ represents:

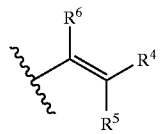

when $R^4$ represents Ar; $R^5$ represents hydrogen, or $C_1$–$C_4$ alkyl; $R^6$ represents hydrogen, or halogen; or an enantiomer thereof, and pharmaceutically acceptable salts thereof.

Preferred embodiments of the invention also include compounds of formula I, wherein A represents:

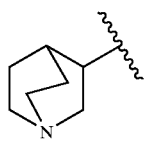

II

D represents oxygen;
$R^2$ represents hydrogen;
$R^3$ represents:

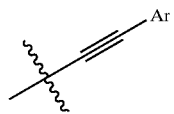

or an enantiomer thereof, and pharmaceutically acceptable salts thereof.

Preferred embodiments of the invention also include compounds of formula I, wherein A represents:

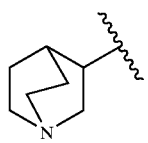

II

D represents oxygen;
$R^2$ represents hydrogen;
$R^3$ represents:

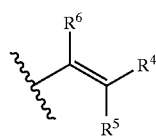

R[4] represents Ar;
R[5] represents hydrogen, or $C_1$–$C_4$ alkyl;
R[6] represents hydrogen, or halogen;
or an enantiomer thereof, and pharmaceutically acceptable salts thereof.

Preferred embodiments of the invention also include compounds of formula I, wherein Ar represents a 5- or 6-membered aromatic or heteroaromatic ring containing zero to three nitrogen atoms, zero or one oxygen atom, and zero or one sulfur atom, or an 8-, 9- or 10-membered fused aromatic or heteroaromatic ring system containing zero to four nitrogen atoms, zero to one oxygen atoms, and zero to one sulfur atoms which may optionally be substituted with one or more substituents selected from the following: hydrogen, halogen, $C_1$–$C_4$ alkyl, $C_2$–$C_4$ alkenyl, $C_2$–$C_4$ alkynyl, aryl, heteroaryl, —$CO_2R^7$, —CN, —$NO_2$, —$NR^8R^9$, —$CF_3$, —$OR^{10}$; or an enantiomer thereof, and pharmaceutically acceptable salts thereof.

Preferred embodiments of the invention also include compounds of formula I, wherein A represents:

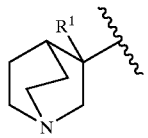

D represents oxygen;
R[1] and R[2] are hydrogen;
R[3] represents:

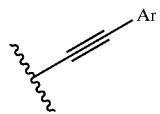

or R[3] represents:

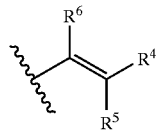

in which:
R[4] represents Ar;
R[5] represents hydrogen or $C_1$–$C_4$ alkyl;
R[6] represents hydrogen or halogen;

Ar represents a 5- or 6-membered aromatic or heteroaromatic ring containing zero to three nitroaen atoms, zero or one oxygen atom, and zero or one sulfur atom, including phenyl, 2-, 3-, or 4-pyridyl, 2- or 3-furanyl, and 2- or 3-thienyl, any of which may optionally be substituted with one or more substituents chosen from among the following: hydrogen, halogen, $C_1$–$C_4$ alkyl, $C_2$–$C_4$ alkenyl, $C_2$–$C_4$ alkynyl, —$CO_2R7$, —CN, —$NO_2$, —$NR^8R^9$, —$CF_3$, —$OR^{10}$; or an enantiomer thereof, and pharmaceutically acceptable salts thereof.

Preferred compounds of formula I include the following:
N-(1-Azabicyclo[2.2.2]oct-3-yl)(E-3-phenylpropenamide);
N-(1-Azabicyclo[2.2.2]oct-3-yl)(3-phenylpropynamide);
N-(1-Azabicyclo[2.2.2]oct-3-yl)[E-3-(2-nitrophenyl)propenamide];
N-(1-Azabicyclo[2.2.2]oct-3-yl)[E-3-(2-nitrophenyl)propenamide];
N-(1-Azabicyclo[2.2.2]oct-3-yl)[E-3-(2-aminophenyl)propenamide];
N-(1-Azabicyclo[2.2.2]oct-3-yl)[Z-3-(2-methoxyphenyl)propenamide];
N-(1-Azabicyclo[2.2.2]oct-3-yl)-N-methyl-(E-3-phenylpropenamide);
N-(1-Azabicyclo[2.2.2]oct-3-yl)[E-2-phenylcyclopropane-1-carboxamide);
N-(1-Azabicyclo[2.2.2]oct-3-yl)(Z-2-fluoro-3-phenylpropenamide);
N-(1-Azabicyclo[2.2.2]oct-3-yl)[E-3-(2-formamidophenyl)propenamide];
N-(1-Azabicyclo[2.2.2]oct-3-yl)[E-3-(4-nitrophenyl)propenamide];
N-(1-Azabicyclo[2.2.2]oct-3-yl)(E-3-(4-aminophenyl)propenamide;
N-(1-Azabicyclo[2.2.2]oct-3-yl)(E-3-(4-formamidophenyl)propenamide];
N-(1-Azabicyclo[2.2.2]oct-3-yl)(Z-3-methyl-3-phenylpropenamide);
N-(1-Azabicyclo[2.2.2]oct-3-yl)[E-3-(4-N-methylaminophenyl)propenamide];
N-(1-Azabicyclo[2.2.2]oct-3-yl)[E-3-(4-N,N-dimethylaminophenyl)propenamide];
N-(1-Azabicyclo[2.2.2]oct-3-yl)(Z-3-phenylpropenamide);
N-(1-Azabicyclo[2.2.2]oct-3-yl)(E-3-methyl-3-phenylpropenamide);
N-(1-Azabicyclo[2.2.2]oct-3-yl)(E-2,3-diphenylpropenamide);
N-(1-Azabicyclo[2.2.2]oct-3-yl)[E-3-(4-methoxyphenyl)propenamide];
N-(1-Azabicyclo[2.2.2]oct-3-yl)[E-2-methyl-3-phenylpropenamide);
N-(1-Azabicyclo[2.2.2]oct-3-yl)[E-3-(2-methylphenyl)propenamide];
N-(1-Azabicyclo[2.2.2]oct-3-yl)[E-3-(3-methoxyphenyl)propenamide];
N-(1-Azabicyclo[2.2.2]oct-3-yl)[E-3-(2-fluorophenyl)propenamide];
N-(1-Azabicyclo[2.2.2]oct-3-yl)[E-3-(4-fluorophenyl)propenarnide];
N-(1-Azabicyclo[2.2.2]oct-3-yl)[E-(2-chlorophenyl)propenarnide];
N-(1-Azabicyclo[2.2.2]oct-3-yl)[E-3-(3-chlorophenyl)propenamide];
N-(1-Azabicyclo[2.2.2]oct-3-yl)[E-3-(4-chlorophenyl)propenamide];
N-(1-Azabicyclo[2.2.2]oct-3-yl)-[E-3-(3,4-dichlorophenyl)propenamide];
N-(1-Azabicyclo[2.2.2]oct-3-yl)-[E-3-(3-bromophenyl)propenamide];
N-(1-Azabicyclo[2.2.2]oct-3-yl)-[E-3-(4-bromophenyl)propenamide];
N-(1-Azabicyclo[2.2.2]oct-3-yl)[E-3-(3-iodophenyl)propenamide];
N-(1-Azabicyclo[2.2.2]oct-3-yl)[E-3-(4-iodophenyl)propenamide];
N-(1-Azabicyclo[2.2.2]oct-3-yl)[E-3-(2-trifluoromethylphenyl)propenamide];

N-(1-Azabicyclo[2.2.2]oct-3-yl)-[E-3-(3-trifluoromethylphenyl)propenamide];
N-(1-Azabicyclo[2.2.2]oct-3-yl)[E-3-(2-furyl)propenamidel;
N-(1-Azabicyclo[2.2.2]oct-3-yl)[E-3-(3-furyl)propenamide];
N-(1-Azabicyclo[2.2.2]oct-3-yl)[E-3-(2-pyridyl)propenamide];
N-(1-Azabicyclo[2.2.2]oct-3-yl)[E-3-(3-pyridyl)propenamide];
N-(1-Azabicyclo[2.2.2]oct-3-yl)[E-3-(4-pyridyl)propenamide];
N-(1-Azabicyclo[2.9.2]oct-3-yl)[E-3-(2-thienyl)propenamide];
N-(1-Azabicyclo[9,2,9]oct-3-yl)[E-3-(3-thienyl)propenamide];
N-(1-Azabicyclo[2.2.2,)oct-3-yl)[E-3-(5-nitro-2-furyl)propenamide];
N-(1-Azabicyclo[2.2.2]oct-3-yl)[E-3-(5-methoxy-3-pyridyl)propenarnide];
N-(1-Azabicyclo[2.2.2]oct-3-yl)[E-3-(5-hydroxy-3-pyridyl)propenarnidel;
N-(1-Azabicyclo[2.2.2]oct-3-yl)[E-3-(4-imidazolyl)propenamide];
N-(endo-8-Aza-8-methylbicyclo[3.2.1]oct-3-yl)(E-3-phenylpropenamide);
N-(exo-8-Aza-8-methylbicyclo[3.2.1]oct-3-yl)(E-3-phenylpropenarnide);

or an enantiomer thereof, and pharmaceutically acceptable salts thereof.

Particularly preferred compounds of formula I include the following:

(R)-N-(1-Azabicyclo[2.2.2]oct-3-yl)(E-3-phenylpropenamide);
(S)-N-(1-Azabicyclo[2.2.2]oct-3-yl)(E-3-phenylpropenamide);
(RS)-N-(1-Azabicyclo[2.2.2]oct-3-yl)(E-3-phenylpropenamide);
(R)-N-(1-Azabicyclo[2.2.2]oct-3-yl)(3-phenylpropynamide);
(S)-N-(1-Azabicyclo[2.2.2]oct-3-yl)(3-phenylpropynamide);
(R)-N-(1-Azabicyclo[2.2.2]oct-3-yl)[E-3-(2-nitrophenyl)propenamide];
(S)-N-(1-Azabicyclo[2.2.2]oct-3-yl)[E-3-(2-nitrophenyl)propenamide];
(RS)-N-(1-Azabicyclo[2.2.2]oct-3-yl)[E-3-(2-nitrophenyl)propenamide];
(RS)-N-(1-Azabicyclo[2.2.2]oct-3-yl)[E-3-(2-aminophenyl)propenamide];
(R)-N-(1-Azabicyclo[2.2.2]oct-3-yl)[E-3-(2-aminophenyl)propenamide];
(R)-N-(1-Azabicyclo[2.2.2]oct-3-yl)[Z-3-(2-methoxyphenyl)propenamide];
(RS)-N-(1-Azabicyclo[2.2.2]oct-3-yl)-N-methyl-(E-3-phenylpropenamide);
(S)-N-(1-Azabicyclo[2.2.2,]oct-3-yl)[E-2-phenylcyclopropane-1-carboxamnide);
(R)-N-(1-Azabicyclo[2.2.2]oct-3-yl)(E-2-phenylcyclopropane-1-carboxamide);
(R)-N-(1-Azabicyclo[2.2.2]oct-3-yl)(Z-2-fluoro-3-phenylpropenamide);
(R)-N-(1-Azabicyclo[2.2.2]oct-3-yl)[E-3-(2-formamidophenyl)propenamide];
(R)-N-(1-Azabicyclo[2.2.2]oct-3-yl)[E-3-(4-nitrophenyl)propenamide];
(R)-N-(1-Azabicyclo[2.2.2]oct-3-yl)(E-3-(4-aminophenyl)propenamide;
(R)-N-(1-Azabicyclo[2.2.2]oct-3-yl)(E-3-(4-formamidophenyl)propenamide];
(R)-N-(1-Azabicyclo[2.2.2]oct-3-yl)(Z-3-methyl-3-phenylpropenamide);
(R)-N-(1-Azabicyclo[2.2.2]oct-3-yl)[E-3-(4-N-methylaminophenyl)propenamide];
(R)-N-(1-Azabicyclo[2.2.2]oct-3-yl)[E-3-(4-N,N-dimethylaminophenyl)propenamide];
(R)-N-(1-Azabicyclo[2.2.2]oct-3-yl)(Z-3-phenylpropenamide);
(R)-N-(1-Azabicyclo[2.2.2]oct-3-yl)(E-3-methyl-3-phenylpropenamide);
(R)-N-(1-Azabicyclo[2.2.2]oct-3-yl)(E-2.3-diphenylpropenamide);
(R)-N-(1-Azabicyclo[2.2.2]oct-3-yl)(E-3-(4-methoxyphenyl)propenamide];
(R)-N-(1-Azabicyclo[2.2.2]oct-3-yl)(E-2-methyl-3-phenylpropenamide);
(S)-N-(1-Azabicyclo[2.2.2]oct-3-yl)(E-2-methyl-3-phenylpropenamide);
(R)-N-(1-Azabicyclo[2.2.2]oct-3-yl)[E-3-(2-methylphenyl)propenamide];
(S)-N-(1-Azabicyclo[2.2.2]oct-3-yl)[E-3-(2-methylphenyl)propenamide];
(RS)-N-(1-Azabicyclo[2.2.2]oct-3-yl)[E-3-(2-methoxyphenyl)propenamide];
(R)-N-(1-Azabicyclo[2.2.2]oct-3-yl)[E-3-(3-methoxyphenyl)propenamide];
(RS)-N-(1-Azabicyclo[2.2.2]oct-3-yl)[E-3-(4-methoxyphenyl)propenamide];
(RS)-N-(1-Azabicyclo[2.2.2]oct-3-yl)[E-3-(2-fluorophenyl)propenamide];
(R)-N-(1-Azabicyclo[2.2.2]oct-3-yl)[E-3-(3-fluorophenyl)propenamide];
(R)-N-(1-Azabicycio[2.2.2]oct-3-yl)[E-3-(4-fluorophenyl)propenamide];
(R)-N-(1-Azabicyclo[2.2.2]oct-3-yl)[E-(2-chlorophenyl)propenamide];
(S)-N-(1-Azabicyclo[2.2.2]oct-3-yl)[E-(2-chlorophenyl)propenamide];
(R)-N-(1-Azabicyclo[2.2.2]oct-3-yl)[E-3-(3-chlorophenyl)propenamide];
(R)-N-(1-Azabicyclo[2.2.2]oct-3-yl)[E-3-(4-chlorophenyl)propenamide];
(R)-N-(1-Azabicyclo[2.2.2]oct-3-yl)-[E-3-(3,4-dichlorophenyl)propenamide];
(R)-N-(1-Azabicyclo[2.2.2]oct-3-yl)-[E-3-(3-bromophenyl)propenamide]
(R)-N-(1-Azabicyclo[2.2.2]oct-3-yl)-[E-3-(4-bromophenyl)propenamide];
(RS)-N-(1-Azabicyclo[2.2.2]oct-3-yl)[E-3-(3-iodophenyl)propenamide];
(RS)-N-(1-Azabicyclo[2.2.2]oct-3-yl)[E-3-(4-iodophenyl)propenamide];
(RS)-N-(1-Azabicyclo[2.2.2]oct-3-yl)[E-3-(2-trifluoromethylphenyl)propenamide];

(R)-N-(1-Azabicyclo[2.2.2]oct-3-yl)-[E-3-(3-trifluoromethylphenyl)propenamide];
(R)-N-(1-Azabicyclo[2.2.2]oct-3-yl)[E-3-(2-furyl)propenamide];
(R)-N-(1-Azabicyclo[2.2.2]oct-3-yl)[E-3-(3-furyl)propenamide];
(R)-N-(1-Azabicyclo[2.2.2]oct-3-yl)[E-3-(2-pyridyl)propenarmide];
(R)-N-(1-Azabicyclo[2.2.2]oct-3-yl)[E-3-(3-pyridyl)propenamide];
(R)-N-(1-Azabicyclo[2.2.2]oct-3-yl)[E-3-(4-pyridyl)propenamide];
(R)-N-(1-Azabicyclo[2.2.2]oct-3-yl)[E-3-(2-thienyl)propenamide];
(R)-N-(1-Azabicyclo[2.2.2]oct-3-yl)[E-3-(3-thienyl)propenamide];
(R)-N-(1-Azabicyclo[2.2.2]oct-3-yl)[E-3-(5-nitro-2-furyl)propenamide];
(R)-N-(1-Azabicyclo[2.2.2]oct-3-yl)[E-3-(5-methoxy-3-pyridyl)propenamide];
(R)-N-(1-Azabicyclo[2.2.2]oct-3-yl)[E-3-(5-hydroxy-3-pyridyl)propenamide];
(R)-N-(1-Azabicyclo[2.2.2]oct-3-yl)[E-3-(4-imidazolyl)propenarnide];
N-(endo-8-Aza-8-methylbicyclo[3.2.1]oct-3-yl)(E-3-phenylpropenamide);
N-(exo-8-Aza-8-methylbicyclo[3.2.1]oct-3-yl)(E-3-phenylpropenarnide), or an enantiomer thereof, and pharmaceutically acceptable salts thereof.

In another aspect of the present invention, there is provided novel compounds according to formula I, with the additional proviso that Ar does not represent 2-, 3-, 4-pyridyl, unsubstituted phenyl or phenyl substituted with one or more substituents selected from $C_1$–$C_4$ alkyl, $C_1$–$C_4$ alkoxy, halogen, phenoxy, hydroxy, $OCOR^{11}$, $NH_2$, $NHCOR^{11}$, and nitro, when:

A represents:

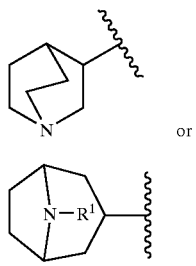

II or

VI $R^3$ represents:

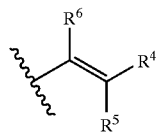

D represents oxygen;
R represents methyl;
$R^2$ and $R^5$ both represent hydrogen;
$R^6$ represents any of hydrogen, $C_1$–$C_4$ alkyl, phenyl, or cyano;

or an enantiomer thereof, and pharmaceutically acceptable salts thereof, which are potent ligands for nicotinic acethylcholine receptors.

In a preferred embodiment of this aspect of the invention, there is provided a compound according to formula I, as defined above, wherein A represents:

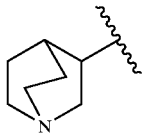

II or an enantiomer thereof, and pharmaceutically acceptable salts thereof.

In another preferred embodiment of this aspect of the invention, there is provided a compound according to formula I, as defined above, wherein A represents:

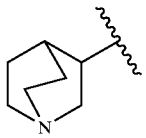

II and $R^6$ represents any of 2-furyl; 3-furyl: 2-thienyl; 3-thienyl: or an enantiomer thereof, and pharmaceutically acceptable salts thereof.

Among these compounds, the following compounds are preferred:

N-(1-Azabicyclo[2.2.2]oct-3-yl)[E-3-(3-trifluoromethylphenyl)propenamide]:
N-(1-Azabicyclo[2.2.2]oct-3-yl)[E-3-(2-furyl)propenamide];
N-(1-Azabicyclo[2.2.2]oct-3-yl)[E-3-(3-furyl)propenamide];
N-(1-Azabicyclo[2.2.2]oct-3-yl)[E-3-(2-thienyl)propenamide];
N-(1-Azabicyclo[2.2.2]oct-3-yl)[E-3-(3-thienyl)propenamide];
N-(1-Aza-3-cyanobicyclo[2.2.2]oct-3-yl)[E-3-phenylpropenamide];
N-(1-Aza-3-methylbicyclo[2.2.2]oct-3-yl)[E-3-phenylpropenamide];
N-(1-Azabicyclo[2.2.2]oct-3-yl)[E-3-(5-nitro-2-furyl)propenamide];
N-(1-Azabicyclo[2.2.2]oct-3-yl)[E-3-(5-methoxy-3-pyridyl)propenamide]:
N-(1-Azabicyclo[2.2.2oct-3-yl)[E-3-(5-hydroxy-3-pyridyl)propenamide];
N-(1-Azabicyclo[2.2.2]oct-3-yl)[E-3-(4-imidazolyl)propenamide];

or an enantiomer and/or pharmaceutically acceptable salts thereof.

Among these compounds, the following compounds are particularly preferred:
(R)-N-(1-Azabicyclo[2.2.2]oct-3-yl)[E-3-(3-trifluoromethylphenyl)propenamide];
(R)-N-(1-Azabicyclo[2.2.2]oct-3-yl)[E-3-(2-furyl)propenamide];
(R)-N-(1-Azabicyclo[2.2.2]oct-3-yl)[E-3-(3-furyl)propenamide];

(R)-N-(1-Azabicyclo[2.2.2]oct-3-yl)[E-3-(2-thienyl)propenamide];

(R)-N-(1-Azabicyclo[2.2.2]oct-3-yl)[E-3-(3-thienyl)propenamide];

N-(1-Aza-3-cyanobicyclo[2.2.2]oct-3-yl)[E-3-phenylpropenamide];

N-(1-Aza-3-methylbicyclo[2.2.2]oct-3-yl)[E-3-phenylpropenamide];

(R)-N-(1-Azabicyclo[2.2.2]oct-3-yl)[E-3-(5-nitro-2-furyl)propenamide];

(R)-N-(1-Azabicyclo[2.2.2]oct-3-yl)[E-3-(5-methoxy-3-pyridyl)propenamide];

(R)-N-(1-Azabicyclo[2.2.2]oct-3-yl)[E-3-(5-hydroxy-3-pyridyl)propenamide];

(R)-N-(1-Azabicyclo[2.2.2]oct-3-yl)[E-3-(4-imidazolyl)propenamide].

Pharmaceutically acceptable derivatives include solvates and salts. For example, the compounds of formula I can form acid addition salts with acids, such as the conventional pharmaceutically acceptable acids, for example, maleic, hydrochloric, hydrobromic, phosphoric, acetic, fumaric, salicylic, citric, lactic, mandelic, tartaric and methanesulfonic acids.

The compounds of the invention have the advantage that they may be less toxic, be more efficacious, be longer acting, have a broader range of activity, be more potent, produce fewer side effects, are more easily absorbed or have other useful pharmacological properties.

Methods of Preparation

In the reaction schemes and text that follow, A, $R^1$, $R^2$, and $R^3$, unless otherwise indicated, are as defined above for formula I. The compounds of formula I may be prepared according to the methods outlined in Scheme 1.

Scheme 1.

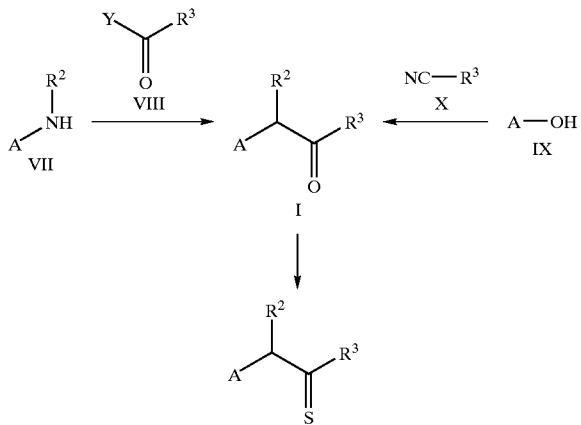

Compounds of formula I wherein D represents oxygen may be prepared from compounds of formula VII by reaction with a compound of formula VIII, wherein Y represents a suitable leaving group, using a suitable acylation procedure. Suitable leaving groups Y include: OH, halogen, OAlkyl. OAryl, OCOAlkyl, OCOAryl, azide. A suitable acylation procedure involves treatment of a compound of formula I with a compound of formula VIII at 0–120° C. in a suitable solvent. The presence of a base, or, when Y=OH, a coupling agent, may also be necessary for the reaction to occur. Suitable bases for the reaction include: 4-(N,N-dimethylamino)pyridine, pyridine, triethylamine, N,N-diisopropylethylamine. The preferred base is N,N-diisopropylethylamine. Suitable coupling agents when Y=OH include: carboduimides, for example 1,3-dicyclohexylcarbodiimide or 1-(3-dimethylaminopropyl-3-ethylcarbodiimide hydrochloride; phosphonium reagents, for example benzotriazol-1-yloxytris(dimethylamino)phosphonium hexafluorophosphate or benzotriazol-1-yloxytripyrrolidinophosphonium hexafluorophosphate; and uronium reagents, for example O-benzotriazol-1-yl-N,N,N',N'-tetramethyluronium tetrafluoroborate. The preferred coupling agent is O-benzotriazol-1-yl-N,N,N',N'-tetramethyluronium tetrafluoroborate. Suitable solvents for the reaction include N,N-dimethylformamide, dimethylsulfoxide. tetrahydrofuran, or chloroform. The preferred solvent is N,N-dimethylformamide. The reaction is preferably performed at a temperature of 0–50° C., and most preferably at a temperature of 20–30° C.

Compounds of formula I wherein D represents oxygen and $R^2$ represents hydrogen may alternatively be prepared from compounds of formula IX by treatment with a nitrile of formula X in a suitable solvent in the presence of a suitable acid. Suitable acids include sulfuric acid, and suitable solvents include acetic acid. The reaction is carried out at a temperature of 0–50° C., and preferably at a temperature of 0–25° C.

Compounds of formula I in which D represents sulfur may be prepared from compounds of formula I in which D represents oxygen by reaction with a suitable sulfide in a suitable solvent. The preferred sulfides are phosphorus sulfides, in particular 4-methoxyphenylthionophosphine sulfide dimer ("Lawesson's Reagent"), and diphosphorus pentasulfide. Suitable solvents for the reaction include aryl hydrocarbon solvents, for example toluene or xylene. The reaction is performed at a temperature of 0–200° C., and preferably at a temperature of 50–180° C.

Compounds of formula VII in which $R^2$ represents an alkyl group may be prepared from compounds of formula VII in which $R^2$ represents hydrogen by a suitable alkylation procedure. Typical alkylation procedures include treatment with an appropriate alkyl halide or sulfonate ester and base, for example sodium hydride, in a suitable solvent, for example DMF, or reductive alkylation using the appropriate aldehyde or ketone together with a suitable reducing agent in an inert solvent. The preferred method is reductive alkylation. Suitable reducing agents include sodium borohydride and sodium cyanoborohydride. The preferred reducing agent is sodium borohydride. Suitable inert solvents include water, methanol or ethanol. The preferred solvent is methanol. The reaction is usually conducted at a temperature of 0–100° C., preferably at 20° C.–65° C.

Compounds of formula VII are commercially available or may be prepared by methods known to one skilled in the art. For example, certain compounds of formula VII may be prepared from compounds of formula IX via a Ritter reaction with a suitable nitrile, followed by hydrolysis of the resulting amide.

Compounds of formula VIII and X are commercially available or may be prepared by methods known to one skilled in the art. See, for example, the methods cited in "Comprehensive Organic Transformations" by R. C. Larock (VCH Publishers, 1989), pages 819–995, and the general references cited on page 823 of the same text.

It will be appreciated by one skilled in the art that certain optional aromatic substituents in the compounds of the invention may be introduced by employing aromatic substitution reactions, or functional group transformations to modify an existing substituent, or a combination thereof. Such reactions may be effected either prior to or immediately following the processes mentioned above, and are included as part of the process aspect of the invention. The reagents and reaction conditions for such procedures are known in the art. Specific examples of procedures which may be employed include, but are not limited to, electrophilic functionalisation of an aromatic ring, for example via nitration, halogenation, or acylation; transformation of a nitro group to an amino group, for example via reduction, such as by catalytic hydrogenation; acylation, alkylation or sulfonylation of an amino or hydroxyl group; replacement of an amino group by another functional group via conversion to an intermediate diazonium salt followed by nuclephilic or free radical substitution of the diazonium salt, or replacement of a halogen by another functional group for example via nucleophilic or catalysed substitution reactions.

Where necessary, hydroxy, amino, or other reactive groups may be protected using a protecting group as described in the standard text "Protecting groups in Organic Synthesis", $3^{rd}$ Edition (1999) by Greene and Wuts.

The above described reactions, unless otherwise noted, are usually conducted at a pressure of about one to about three atmospheres, preferably at ambient pressure (about one atmosphere). Unless otherwise stated, the above described reactions are conducted under an inert atmosphere, preferably under a nitrogen atmosphere.

The compounds of the invention and intermediates may be isolated from their reaction mixtures by standard techniques.

Acid addition salts of the compounds of formula I which may be mentioned include salts of mineral acids, for example the hydrochloride and hydrobromide salts; and salts formed with organic acids such as formate, acetate, maleate, benzoate, tartrate, and fumarate salts.

Acid addition salts of compounds of formula I may be formed by reacting the free base or a salt, enantiomer or protected derivative thereof, with one or more equivalents of the appropriate acid. The reaction may be carried out in a solvent or medium in which the salt is insoluble or in a solvent in which the salt is soluble, e.g., water, dioxane, ethanol, tetrahydrofuran or diethyl ether, or a mixture of solvents, which may be removed in vacuum or by freeze drying. The reaction may be a metathetical process or it may be carried out on an ion exchange resin.

The compounds of formula I exist in tautomeric or enantiomeric forms, all of which are included within the scope of the invention. The various optical isomers may be isolated by separation of a racemic mixture of the compounds using conventional techniques, e.g. fractional crystallization, or chiral HPLC. Alternatively the individual enantiomers may be made by reaction of the appropriate optically active starting materials under reaction conditions which will not cause racemization.

Pharmaceutical Compositions

A further aspect of the invention relates to a pharmaceutical composition for treating or preventing a condition or disorder as exemplified below arising from dysfunction of nicotinic acetylcholine receptor neurotransmission in a mammal, preferably a human, comprising an amount of a compound of formula I, an enantiomer thereof or a pharmaceutically acceptable salt thereof, effective in treating or preventing such disorder or condition and an inert pharmaceutically acceptable diluent or carrier.

A condition or disorder arising from dysfunction of nicotinic acetylcholine receptor neurotransrnission in a mammal, preferably a human, may be psychotic disorders or intellectual impairment disorders or diseases or conditions in which activation of the $\alpha 7$ nicotinic receptor is beneficial. Examples of such conditions, diseases or disorders include Alzheimer's disease, learning deficit, cognition deficit, attention deficit, memory loss, Attention Deficit Hyperactivity Disorder, anxiety, schizophrenia, mania or manic depression, Lewy Body Dementia, Parkinson's disease, Huntington's disease, Tourette's syndrome, neurodegenerative disorders in which there is loss of cholinergic synapse, jetlag, cessation of smoking, nicotine addiction including that resulting from exposure to products containing nicotine, pain, or ulcerative colitis.

For the above-mentioned uses the dosage administered will, of course, vary with the compound employed, the mode of administration and the treatment desired. However, in general, satisfactory results are obtained when the compounds of the invention are administered at a daily dosage of from about 0.1 mg to about 20 mg per kg of animal body weight, preferably given in divided doses 1 to 4 times a day or in sustained release form. For man, the total daily dose is in the range of from 5 mg to 1,400 mg, more preferably from 10 mg to 100 mg, and unit dosage forms suitable for oral administration comprise from 2 mg to 1,400 mg of the compound admixed with a solid or liquid pharmaceutical carrier or diluent.

The compounds of formula I, or an enantiomer thereof, and pharmaceutically acceptable salts thereof, may be used on their own or in the form of appropriate medicinal preparations for enteral or parenteral administration. According to a further aspect of the invention, there is provided a pharmaceutical composition including preferably less than 80% and more preferably less than 50% by weight of a compound of the invention in admixture with an inert pharmaceutically acceptable diluent or carrier.

Examples of diluents and carriers are:

for tablets and dragees: lactose, starch, talc, stearic acid; for capsules: tartaric acid or lactose;

for injectable solutions: water, alcohols, glycerin, vegetable oils; for suppositories: natural or hardened oils or waxes.

There is also provided a process for the preparation of such a pharmaceutical composition, which comprises mixing the ingredients.

Utility

One aspect of the invention is the use of a compound according to the invention, an enantiomer thereof or a pharmaceutically acceptable salt thereof, in the manufacture of a medicament for the treatment or prophylaxis of one of the below mentioned diseases or conditions: and a method of treatment or prophylaxis of one of the above mentioned diseases or conditions, which comprises administering a therapeutically effective amount of a compound according to the invention, or an enantiomer thereof or a pharmaceutically acceptable salt thereof, to a patient.

Compounds to be used according to the invention are agonists of nicotinic acetylcholine receptors. While not being limited by theory, it is believed that agonists of the $\alpha_7$ nAChR (nicotinic acetylcholine receptor) subtype should be useful in the treatment or prophylaxis of psychotic disorders and intellectual impairment disorders, and have advantages over compounds which are or are also agonists of the $\alpha_7$ nAChR subtype. Therefore, compounds which are selective for the $\alpha_7$ nAChR subtype are preferred. The use of compounds of the invention is indicated as pharmaceuticals, in particular in the treatment or prophylaxis of psychotic disorders and intellectual impairment disorders. Examples of psychotic disorders include schizophrenia, mania or manic depression, and anxiety. Examples of intellectual impairment disorders include Alzheimer's disease, Lewy Body Dementia, learning deficit, cognition deficit, attention deficit, memory loss, and Attention Deficit Hyperactivity Disorder. The compounds of the invention may also be useful as analgesics in the treatment of pain (including chronic pain) and in the treatment or prophylaxis of Parkinson's disease, Huntington's disease, Tourette's syndrome, and neurodegenerative disorders in which there is loss of cholinergic synapses. The compounds may further be indicated for the treatment or prophylaxis of jetlag, for use in inducing the cessation of smoking, and for the treatment or prophylaxis of nicotine addiction (including that resulting from exposure to products containing nicotine).

It is also believed that compounds according to the invention are useful in the treatment and prophylaxis of ulcerative colitis.

Pharmacology

The pharmacological activity of the compounds of the invention may be measured in the tests set out below:

Test A—Assay for Affinity at $\alpha_7$ nAChR Subtype $_{125}$I-α-Bungarotoxin (BTX) binding to rat hippocampal membranes. Rat hippocampi were homogenized in 20 volumes of cold homogenization buffer (HB: concentrations of constituents (mM): tris(hydroxymethyl)aminomethane 50; $MgCl_2$ 1; NaCl 120; KCl 5: pH 7.4). The homogenate was centrifuged for 5 minutes at 1000 g, the supernatant was saved and the pellet re-extracted. The pooled supernatants were centrifuged for 20 minutes at 12000 g, washed, and resuspended in HB. Membranes (30–80 μg) were incubated with 5 nM [$^{125}$I]α-BTX, 1 mg/mL BSA (bovine serum albumin), test drug, and either 2 mM $CaCl_2$ or 0.5 mM EGTA [ethylene glycol-bis(β-aminoethylether)] for 2 hours at 21° C., and then filtered and washed 4 times over Whatman glass fibre filters (thickness C) using a Brandel cell harvester. Pretreating the filters for 3 hours with 1% (BSA/0.01% PEI (polyethyleneimine) in water was critical for low filter blanks (0.07% of total counts per minute). Nonspecific binding was described by 100 μM (−)-nicotine, and specific binding was typically 75%.

Test B—Assay for Affinity to the $\alpha_4$ nAChR Subtype

[$^3$H]-(−)-nicotine binding. Using a procedure modified from Martino-Barrows and Kellar (Mol Pharm (1987) 31:169–174), rat brain (cortex and hippocampus) was homogenized as in the [$_{125}$I]α-BTX binding assay, centrifuged for 20 minutes at 12,000×g, washed twice, and then resuspended in HB containing 100 μM diisopropyl fluorophosphate. After 20 minutes at 4° C., membranes (approximately 0.5 mg) were incubated with 3 nM [3H]-(−)-niconine, test drug, 1 μM atropine, and either 2 mM $CaCl_2$ or 0.5 mM EGTA for 1 hour at 4° C., and then filtered over Whatman glass fibre filters (thickness C) (pretreated for 1 hour with 0.5% PEI) using a Brandel cell harvester. Nonspecific binding was described by 100 μm carbachol, and specific binding was typically 84%.

Binding Data Analysis for Tests A and B $IC_{50}$ values and pseudo Hill coefficients ($n_H$) were calculated using, the non-linear curve fitting, program ALLFIT (DeLean A, Munson P J and Rodbard D (1977) Am. J. Physiol., 235:E97–E102). Saturation curves were fitted to a one site model, using the non-linear regression program ENFITTER (Leatherbarrow, R. J. (1987)), yielding $K_D$ values of 1.67 and 1.70 nM for the $^{125}$I-α-BTX and [$^3$H]-(−)-nicotine ligands respectively. $K_i$ values were estimated using the general Cheng-Prusoff equation:

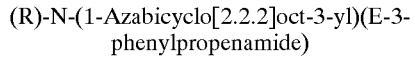

where a value of n=1was used whenever $n_H$<1.5 and a value of n=2 was used when $n_H \geq 1.5$. Samples were assayed in triplicate and were typically ±5%. $K_i$ values were determined using 6 or more drug concentrations. The compounds of the invention are compounds with binding affinities ($K_i$) of less than 10 μM in either Test A or Test B, indicating that they are expected to have useful therapeutic activity.

The use of compounds of the invention have the advantage that they may be less toxic, be more efficacious, be longer acting, have a broader range of activity, be more potent, produce fewer side effects, are more easily absorbed or have other useful pharmacological properties.

GENERAL EXPERIMENTAL PROCEDURES

Commercial reagents were used without further purification. Mass spectra were recorded using either a Hewlett Packard 5988A or a MicroMass Quattro-1 Mass Spectrometer and are reported as m/z for the parent molecular ion. Room temperature refers to 20–25° C.

EXAMPLES

The following examples are preferred non-limiting examples embodying preferred aspects of the invention.

Example 1

(R)-N-(1-Azabicyclo[2.2.2]oct-3-yl)(E-3-phenylpropenamide)

(R)-1-Azabicyclo[2.2.2]oct-3-ylamine dihydrochloride (7.5 g, 0.038 moles) and E-3-phenylpropenoic acid (5.6 g, 0.038 moles) were combined in anhydrous N,N-dimethylformarnide (570 mL) under nitrogen atmosphere. The resulting mixture was stirred while adding 1-hydroxybenzotriazole monohydrate (5.8 g, 0.0378 moles) O-benzotriazol-1-yl-N,N,N',N'-tetramethyluronium tetrafluoroborate (12.1 g, 0.038 moles) and N,N-diisopropylethylamine (26.4 mL) were added. The solution was stirred at ambient temperature for 6 h and then placed in a freezer overnight. The solution was concentrated in vacuo and the residue was taken up in chloroform (360 mL) and washed with aqueous sodium hydroxide (1 M, 360 mL). The basic layer was extracted twice more with chloroform and the organic layers were combined, dried ($MgSO_4$), and concentrated in vaciuo. The compound was then purified on a flash silica gel column with a 5–20% methanol/chloroform/ammonium hydroxide gradient. The hydrochloride salt was prepared from isopropanol and ethyl acetate, giving 9.5 g of slightly off-white powder; MS (ES$^+$) 257 (MH$^+$).

Example 2

(S)-N-(1-Azabicyclo[2.2.2]oct-3-yl)(E-3-phenylpropenamide)

Prepared as free base by a method analogous to that described in Example 1 from (S)-1-azabicyclo[2.2.2]oct-3-

Example 3

(RS)-N-(1-Azabicyclo[2.2.2,]oct-3-yl)(E-3-phenylpropenamide)

Prepared as free base by a method analogous to that described in Example 1 from (RS)-1-azabicyclo[2.2.2]oct-3-ylamine dihydrochloride and E-3-phenylpropenoic acid; MS (ES$^+$) 257 (MH$^+$).

Example 4

(R)-N-(1-Azabicyclo[2.2.2]oct-3-yl)(3-phenylpropynamide)

Prepared as a free base by a method analogous to that described in Example 1 from (R)-1-azabicyclo[2.2.2]oct-3-ylamine dihydrochloride and 3-phenylpropynoic acid; MS (ES$^+$) 255 (MH$^+$).

Example 5

(S)-N-(1-Azabicyclo[2.2.2]oct-3-yl)(3-phenylnropynamide)

Prepared as a free base by a method analogous to that described in Example 1 from (S)-1-azabicyclo[2.2.2]oct-3-ylamine dihydrochloride and 3-phenylpropynoic acid; MS (ES$^+$) 255 (MH$^+$).

Example 6

(R)-N-(1-Azabicyclo[2.2.2]oct-3-yl)[E-3-(2-nitrophenyl)propenamide]

Prepared as a free base by a method analogous to that described in Example 1 from (R)-1-azabicyclo[2.2.2]oct-3-ylamine dihydrochloride and E-3-(2-nitrophenyl)propenoic acid; MS (ES$^+$) 302 (MH$^+$).

Example 7

(S)-N-(1-Azabicyclo[2.2.2]oct-3-yl)[E-3-(2-nitrophenyl)propenamide]

Prepared as a free base by a method analogous to that described in Example 1 from (S)-1-azabicyclo[2.2.2]oct-3-ylamine dihydrochloride and E-3-(2-nitrophenyl)propenoic acid as a solid; MS (ES$^+$) 302 (MH$^+$).

Example 8

(RS)-N-(1-Azabicyclo[2.2.2]oct-3-yl)[E-3-(2-nitrophenyl)propenamide]

Prepared as a free base by a method analogous to that described in Example 1 from (RS)-1-azabicyclo[2.2.2]oct-3-ylamine dihydrochloride and E-3-(2-nitrophenyl)propenoic acid as a solid; MS (ES$^+$) 302 (MH$^+$).

Example 9

(RS)-N-(1-Azabicyclo[2.2.2]oct-3-yl)[E-3-(2-aminolphenyl)propenamide]

(RS)-N-(1-Azabicyclo[2.2.2]oct-3-yl)[E-3-(2-nitrophenyl)propenamide] (0.42g, 0.014 moles) prepared was suspended in acetone (4.2 mL) and ammonium chloride (0.15 g, 0.028 moles) in water (2.1 mL) was added. The clear solution was brought to reflux using an oil bath, and then removed from heating while zinc dust (0.42 g, 0.063 moles) was added. The reaction was held at reflux for one hour, at which point the conversion was complete by thin layer chromatography. The suspension was diluted with chloroform and saturated sodium bicarbonate, and decanted from the solid zinc. The layers were separated and the aqueous layer was extracted twice more with chloroform. The combined layers were dried (MgSO$_4$) and evaporated. The maleate salt was prepared in isopropanol. The solvent was decanted and the orange deliquescent solid was transferred with methanol and stripped to give a foamy orange class; MS (ES$^+$) 272 (MH$^+$).

Example 10

(R)-N-(1-Azabicyclo[2.2.2]oct-3-yl)[E-3-(2-aminophenyl)propenamide]

Prepared by a method analogous to that described in Example 9 from (R)-N-(1-azabicyclo[2.2.2]oct-3-yl)[E-3-(2-nitrophenyl)propenamide]; MS (ES$^+$) 272 (MH$^+$).

Example 11

(R)-N-(1-Azabicyclo[2.2.2,]oct-3-yl)[Z-3-(2-methoxyphenyl)propenamide]

Prepared as a free base by a method analogous to that described in Example 1 from (R)-1-azabicyclo[2.2.2]oct-3-ylamine dihydrochloride and Z-3-(2-methoxyphenyl)propenoic acid; MS (ES$^+$) 287 (MH$^+$).

Example 12

(RS)-N-(1-Azabicyclo[2.2.2]oct-3-yl)-N-methyl-(E-3-phenylipropenamide)

(RS)-N-(1-Azabicyclo[2.2.2]oct-3-yl)(E-3-phenylpropenamide) (0.15 g$_1$ 0.059 moles) was suspended in anhydrous tetrahydrofuran under nitrogen atmosphere. The reaction mixture was cooled with an ice bath while commercial 1.0M borane/tetrahydrofuran complex (0.59 mL) was added dropwise by syringe. The suspension dissolved immediately and the solution was stirred at 0° C. for one hour. The reaction was carefully quenched by adding water (2 mL) with cooling. The reaction was then diluted with brine and methylene chloride. The layers were separated and the aqueous layer was extracted twice more with methylene chloride. The combined organic layers were dried (MgSO$_4$) and evaporated in vaciuo. Sodium hydride (28 mg, 0.00071 moles) was suspended in anhydrous N,N-dimethylformamide (2 mL) under nitrogen. The crude borane complex was dissolved in N,N-dimethylformamide (1 mL) and added dropwise. The reaction was stirred at room temperature for 30 minutes and then the methyl iodide (55µL, 0.000885 moles) was added by syringe. After stirring 2½ h the reaction was cooled with an ice bath and quenched with water (1 mL). The suspension was diluted with saturated sodium bicarbonate and ethyl acetate and the layers were separated. The aqueous layer was extracted twice more and the organic layers were combined, dried (MgSO$_4$), and concentrated in vacito. The crude complex was dissolved in acetone (1.6 mL) and water (0.27 mL) was added. The reaction was cooled with an ice bath and aqueous hydrogen bromide (0.27 mL) was added dropwise. The reaction was stirred at 0° C. Additional hydrogen bromide (0.27 mL) was added after 5 h but no further change was detected by thin layer chromatography. The acetone was removed in vaciio and chased with one portion of methanol and three of ethanol. The crude was triturated first with ethanol and then ether. Two phases resulted, and the lower was separated and washed with more ether, which was decanted. The remainder of the solvent was removed in vacuo. The yellow semi-solid was transferred using methanol and this was removed in vacuo and chased with two portions if ether. Yielded 0.15 g; MS (ES$^+$) 271 (MH$^+$).

Examples 13 and 14

(S)-N-(1-Azabicyclor]2.2.2]oct-3-yl)(E-2-phenylcyclopropane-1-carboxamide)

Prepared as free bases by a method analogous to that described in Example 1 from (S)-1-azabicyclo[2.2.2]oct-3-ylamine dihydrochloride and trans-2-phenylcyclopropane-1-carboxylic acid. The diastereomers could be separated by chromatography on silica gel using a 10–30% methanol/chloroform/ammonium hydroxide gradient; both MS (ES$^+$) 271 (MH$^+$).

Examples 15 and 16

(R)-N-(1-Azabicyclo[2.2.2]oct-3-yl)(E-2-phenylcyclopropane-1-carboxamide)

Prepared as free bases by a method analogous to that described in Example 1 from (R)-1-azabicyclo[2.2.2]oct-3-ylaamine dihydrochloride and trans-2-phenylcyclopropane-1-carboxylic acid. The diastereomers could be separated by chromatography on silica gel using a 10–30% methanol/chloroform/ammonium hydroxide gradient; both MS (ES$^+$) 271 (MH$^+$).

Example 17

(R)-N-(1-Azabicyclo[2.2.2]oct-3-yl)(Z-2-fluoro-3-phenylpropenamide)

Prepared as free base by a method analogous to that described in Example 1 from (R)-1-azabicyclo[2.2.2]oct-3-ylamine dihydrochloride and Z-2-fluoro-3-phenylpropenoic acid; MS (ES$^+$) 275 (MH$^+$).

Example 18

(R)-N-(1-Azabicyclo[2.2.2]oct-3-yl)[E-3-(2-formamidophenyl)propenamide]

Formic acid (98%, 2.9 mL) and acetic anhydride (1.0 mL) were combined under an inert atmosphere while cooling with a cold water bath. (R)-N-(1-Azabicyclo[2.2.2]oct-3-yl)(E-3-(2-aminophenyl)propenamide) (0.16 g, 0.00059 moles) was added and the reaction was stirred for three days at room temperature. The solution was poured into saturated sodium carbonate and more solid carbonate was added until the solution was basic. The aqueous layer was extracted four times with chloroform. The organic extracts were combined, dried (MgSO$_4$), and concentrated in vacuo. The product was transferred using chloroform and this was stripped and chased with two portions of ether. The white solid was dried at room temperature with high vacuum, giving 64 mg; MS (ES$^+$) 300 (MH$^+$).

Example 19

(R)-N-(1-Azabicyclo[2.2.2]oct-3-yl)[E-3-(4-nitrophenyl)propenamide]

Prepared as free base by a method analogous to that described in Example 1 from (R)-1-azabicyclo[2.2.2]oct-3-ylamine dihydrochloride and E-3-(4-nitrophenyl)propenoic acid; MS (ES$^+$) 302 (MH$^+$).

Example 20

(R)-N-(1-Azabicyclo[2.2.2]oct-3-yl)[E-3-(4-aminophenyl)proipenamide]

Prepared by a method analogous to Example 9 from (R)-N-(1-Azabicyclo[2.2.2]oct-3-yl)[E-3-(4-nitrophenyl)propenamide]; MS (ES$^+$) 272 (MH$^+$).

Example 21

(R)-N-(1-Azabicyclo[2.2.2]oct-3-yl)[E-3-(4-formamidophenyl)propenamide]

Prepared as free base by a method analogous to that described in Example 18 from (R)-N-(1-azabicyclo[2.2.2]oct-3-yl)(E-3-(4-aminophenyl)propenamide]; MS (ES$^+$) 300 (MH$^+$).

Example 22

(R)-N-(1-Azabicyclo[2.2.2]oct-3-yl)(Z-3-methyl-3-phenylpropenamide)

(A) Z-3-Methyl-3-phenylpropvnoic Acid

Copper(I) iodide (1.1 g, 0.006 moles) was suspended in anhydrous ether (20 mL) and the resulting suspension was kept below −10° C. and stirred protected from light while commercial 1.0M methyl lithium solution (6 mL) was slowly added dropwise. The white suspension was stirred at −10° C. for 30 minutes while the solid dissolved. 3-Phenylpropynoic acid (0.44 g, 0.003 moles) was added in three portions at −60° C. The reaction mixture was then stirred at −10° C. for 90 min and was then poured into dilute aqueous hydrochloric acid. Chloroform was added and the resulting emulsion was filtered through diatomaceous earth, and the phases were then separated. The aqueous layer was extracted three more times with chloroform. The organic layers were combined, dried (MgSO$_4$), and concentrated. The crude product was dried under high vacuum and used without further purification.

(B) (R)-N-(1-Azabicyclo[2.2.2]oct-3-yl)(Z-3-methyl-3-phenylpropenamide)

Prepared as a free base by a procedure analogous to that described in Example 1 from (R)-1-azabicyclo[2.2.2]oct-3-ylamine dihydrochloride and Z-3-methyl-3-phenylpropenoic acid; MS (ES$^+$) 271 (MH$^+$).

Example 23

(R)-N-(1-Azabicyclo[2.2.2]oct-3-yl)[E-3-(4-N-methylaminophenyl)propenamide]

Sodium metal (0.1 g, 0.0043 moles) was added in two portions to dry methanol (2 mL) stirred at 0° C. under nitrogen. After 20 min, (R)-N-(1-azabicyclo[2.2.2]oct-3-yl)[E-3-(4-aminophenyl)propenamide] (0.27 g, 0.001 moles) in methanol was added followed by paraformaldehyde (0.18 g, 0.006 moles), and the resulting solution was stirred at room temperature overnight. The reaction was heated at 50° C. for 4 h then sodium borohydride (0.10 g, 0.0028 moles) was added and the solution was heated under reflux for 2 h. The reaction mixture was allowed to cool and aqueous potassium hydroxide (1 M, 0.8 mL) was added. After the resulting mixture had been stirred at room temperature for 1 h, the solution was concentrated in vacuo, and the residue was partitioned between water and chloroform. The aqueous layer was extracted three times more with chloroform. The organic layers were combined, dried (MgSO$_4$), and concentrated in vacuo. The material was purified first by solid phase extraction on silica using a 10–40% ammoniated methanol/chloroform gradient, and then by reverse phase HPLC on a Waters Bondapak® C$_{18}$ column using a gradient of 10–60% acetonitrile and 0.1% aqueous trifluoroacetic acid as the eluent. The free base was recovered by neutralization and extraction, yielding 45 mg of a yellow powder; MS (ES$^+$) 286 (MH$^+$).

Example 24

(R)-N-(1-Azabicyclo[2.2.2]oct-3-yl)[E-3-(4-N,N-dimethylaminophenyl)propenamide]

Sodium cyanoborohydride (0.19 g, 0.003 mol) and anhydrous zinc chloride (0.21 g, 0.0015 moles) were combined in anhydrous methanol. The mixture was stirred for 5 min and (R)-N-(1-azabicyclo[2.2.2]oct-3-yl)[E-3-(4-aminophenyl)propenamide] (0.27 g, 0.001 moles) was dissolved in methanol (3 mL) was added, followed by paraformaldehyde (0.18 g, 0.006 moles). The reaction mixture was stirred at room temperature overnight. The methanol was concentrated in vaciio and the residue was taken up in 1M sodium hydroxide (20 mL). The aqueous layer was extracted three times with chloroform and these layers were combined, dried (MgSO$_4$) and evaporated in vaciuo. The material was purified first by solid phase extraction on silica using a 10–40% ammoniated methanol/chloroform gradient, and then by reverse phase HPLC on a Waters Bondapak® C$_{18}$ column using a gradient of 10–60% acetonitrile and 0.1% aqueous trifluoroacetic acid as the eluent. The free base was recovered by neutralization and extraction, yielding 12 mg of yellow powder; MS (ES$^+$) 300 (MH$^+$).

Example 25

(R)-N-(1-Azabicyclo[2.2.2]oct-3-yl)(Z-3-phenylpropenamide)

(A) Z-3-Phenylpropenoic Acid

Nickel (II) acetate tetrahydrate (0.16 g, 0.00063 moles) was dissolved in ethanol (6.3 mL) and placed under hydrogen atmosphere. The green solution was stirred rapidly while sodium borohydride (0.024 g, 0.00063 moles) in ethanol (0.63 mL) was added. The deep purple solution was then treated with ethylene diamine (0.42 mL, 0.0063 moles) followed by 3-phenylpropynoic acid (0.73 g, 0.005 moles). The reaction was stirred under hydrogen for 5 hours. The hydrogen was displaced with nitrogen and the suspension was filtered through diatomaceous earth to remove the catalyst. The filtrate was concentrated in vacuo. The residue was taken up in chloroform and water, and concentrated hydrochloric acid was added to acidify the aqueous layer. The layers were separated and the acidic layer was extracted three times more with chloroform. The organic layers were combined and concentrated. The material was purified by reverse phase HPLC on a Waters Bondapak® C$_{18}$ column using a gradient of 10–40% acetonitrile and 0.25% aqueous trifluoroacetic acid as the eluent to give a white solid (0.51 g).

(B) (R)-N-(1-Azabicyclo[2.2.2]oct-3-yl)(Z-3-phenylpropenamide)

Prepared as a free base by a method analogous to that described in Example 1 from (R)-1-azabicyclo[2.2.2]oct-3-ylamine dihydrochloride, and Z-3-phenylpropenoic acid; MS (ES$^+$) 257 (MH$^+$).

Example 26

(R)-N-(1-Azabicyclo[2.2.2]oct-3-yl)(E-3-methyl-3-phenylpropenamide)

(A) E-3-Methyl-3-phenylpropenoic Acid

A complex of copper (I) bromide (1.72 g, 0.12 moles) and lithium bromide (1.0 g, 0.012 moles) was prepared in anhydrous tetrahydrofuran and cooled to –50° C. Commercial methyl magnesium bromide (3.0 M in ether; 4 mL) was added dropwise. The suspension was stirred at –50° C. for 15 min, then 3-phenylpropynoic acid (0.44 g, 0.003 moles) was added in three portions. The mixture was stirred at –50° C. for 15 minutes and then was directly warmed to 30° C. with a warm water bath. After stirring for one hour the reaction mixture was poured into saturated ammonium chloride. The solution was acidified by slowly adding concentrated hydrochloric acid and then was extracted four times with chloroform. The organic layers were combined, dried (MgSO$_4$), and concentrated in vacuo. The material was purified by reverse phase HPLC on a Waters Bondapak® C$_{18}$ column using a gradient of 20–60% acetonitrile and 0.25% aqueous trifluoroacetic acid as the eluent to give a colourless solid (0.14 g).

(B) (R)-N-(1-Azabicyclo[2.2.2]oct-3-yl)(E-3-methyl-3-phenylpropenamide)

Prepared as a free base by a method analogous to that described in Example 1 from (R)-1-azabicyclo[2.2.2]oct-3-ylamine dihydrochloride and E-3-methyl-3-phenylpropenoic acid, giving a light tan solid; MS (ES$^+$) 271 (MH$^+$).

Example 27

(R)-N-(1-Azabicyclo[2.2.2]oct-3-yl)(E-2,3-diphenylpropenamide)

Prepared as free base by a method analogous to that described in Example 1 from (R)-1-azabicyclo[2.2.2]oct-3-ylamine dihydrochloride and E-2,3-diphenylpropenoic acid; MS (ES$^+$) 333 (MH$^+$).

Example 28

(R)-N-(1-Azabicyclo[2.2.2]oct-3-yl)[E-3-(4-methoxyphenyl)Propenamide]

Prepared as free base by a method analogous to that described in Example 1 from (R)-1-azabicyclo[2.2.2]oct-3-ylamine dihydrochloride and E-3-(4-methoxy)phenylpropenoic acid; MS (ES$^+$) 287 (MH$^+$).

Example 29

(R)-N-(1-Azabicyclo[2.2.2]oct-3-yl)(E-2-methyl-3-phenylpropenamide)

Prepared as free base by a method analogous to that described in Example 1 from (R)-1-azabicyclo[2.2.2]oct-3-ylamine dihydrochloride and E-2-methyl-3-phenylpropenoic acid; MS (ES$^+$) 271 (MH$^+$).

Example 30

(S)-N-(1-Azabicyclo[2.2.2]oct-3-yl)(E-2-methyl-3-phenylpropenamide)

Prepared as free base by a method analogous to that described in Example 1 from (S)-1-azabicyclo[2.2.2]oct-3-ylamine dihydrochloride and E-α-methyl-3-phenylpropenoic acid; MS (ES$^+$) 271 (MH$^+$).

Example 31

(R)-N-(1-Azabicyclo[2.2.2]oct-3-yl)[E-(2-methylphenyl)prolenamide]

Prepared as a free base by a method analogous to that described in Example 1 from (R)-1-azabicyclo[2.2.2]oct-3-ylamine dihydrochloride and E-3-(2-methylphenyl)propenoic acid; MS (ES$^+$) 271 (MH$^+$).

Example 32

(S)-N-(1-Azabicyclo[2.2.2]oct-3-yl)[E-(2-methylphenyl)propenamide]

Prepared as a free base by a method analogous to that described in Example 1 from (S)-1-azabicyclo[2.2.2]oct-3-ylamine dihydrochloride and E-3-(2-methylphenyl)propenoic acid; MS (ES$^+$) 271 (MH$^+$).

Example 33

(RS)-N-(1-Azabicyclo[2.2.2]oct-3-yl)[E-(2-methoxyphenyl)pronenamide]

Prepared as a free base by a method analogous to that described in Example 1 from racemic 1-azabicyclo[2.2.2]oct-3-ylamine dihydrochloride and E-3-(2-methoxyphenyl)propenoic acid; MS (ES$^+$) 287 (MH$^+$).

Example 34

(R)-N-(1-Azabicyclo[2.2.2]oct-3-yl)[E-3-(3-methoxyphenyl)propenamide]

Prepared as a free base by a method analogous to that described in Example 1 from (R)-1-azabicyclo[2.2.2]oct-3-ylamine dihydrochloride and E-3-(3-methoxyphenyl)propenoic acid; the compound was purified by chromatography on silica gel using ammoniated methanol/chloroform mixtures as the eluent; MS (ES$^+$) 287 (MH$^+$).

Example 35

(RS)-N-(1-Azabicyclo[2.2.2]oct-3-yl)[E-(4-methoxyphenyl)propenamide]

Prepared as a free base by a method analogous to that described in Example 1 from racemic 1-azabicyclo[2.2.2]oct-3-ylamine dihydrochloride and E-3-(4-methoxyphenyl)propenoic acid; MS (ES$^+$) 287 (MH$^+$).

Example 36

(RS)-N-(1-Azabicyclo[2.2.2]oct-3-yl)[E-(2-fluorophenyl)pronenamide]

Prepared as a free base by a method analogous to that described in Example 1 from racemic 1-azabicyclo[2.2.2]oct-3-ylamine dihydrochloride and E-3-(2-fluorophenyl)propenoic acid; MS (ES$^+$) 275 (MH$^+$).

Example 37

(R)-N-(1-Azabicyclo[2.2.2]oct-3-yl)[E-3-(3-fluoronhenyl)pronenamide]

Prepared by a method analogous to that described in Example 1 from (R)-1-azabicyclo[2.2.2]oct-3-ylamine dihydrochloride and E-3-(3-fluorophenyl)propenoic acid; the compound was purified by chromatography on silica gel using ammoniated methanol/chloroform mixtures as the eluent; MS (ES$^+$) 275 (MH$^+$).

Example 38

(R)-N-(1-Azabicyclo[2.2.2]oct-3-yl)[E-3-(4-fluorophenyl)propenamide]

Prepared as a free base by a method analogous to that described in Example 1 from (R)-1-azabicyclo[2.2.2]oct-3-ylamine dihydrochloride and E-3-(4-fluorophenyl)propenoic acid; the compound was purified by chromatography on silica gel using ammoniated methanol/chloroform mixtures as the eluent; MS (ES$^+$) 275 (MH$^+$).

Example 39

(R)-N-(1-Azabicyclo[2.2.2]oct-3-yl)[E-3-(2-chlorophenyl)propenamide]

Prepared as a free base by a method analogous to that described in Example 1 from (R)-1-azabicyclo[2.2.2]oct-3-ylamine dihydrochloride and E-3-(2-chlorophenyl)propenoic acid; MS (ES$^+$) 291 and 293 (MH$^+$).

Example 40

(S)-N-(1-Azabicyclo[2.2.2]oct-3-yl)[E-3-(2-chlorophenyl)pronenamide]

Prepared as a free base by a method analogous to that described in Example 1 from (S)-1-azabicyclo[2.2.2]oct-3-ylamine dihydrochloride and E-3-(2-chlorophenyl)propenoic acid; MS (ES$^+$) 291 and 293 (MH$^+$).

Example 41

(R)-N-(1-Azabicyclo[2.2.2]oct-3-yl)[E-3-(3-chlorophenyl)propenamide]

Prepared as a free base by a method analogous to that described in Example 1 from (R)-1-azabicyclo[2.2.2]oct-3-ylamine dihydrochloride and E-3-(3-chlorophenyl)propenoic acid; the compound was purified by chromatography on silica gel using amrnmoniated methanol/chloroform mixtures as the eluent; MS (ES$^+$) 291, 293 (MH$^+$).

Example 42

(R)-N-(1-Azabicyclo[2.2.2]oct-3-yl)[E-3-(4-chlorophenyl)propenamide]

Prepared as a free base by a method analogous to that described in Example 1 from (R)-1-azabicyclo[2.2.2]oct-3-ylamine dihydrochloride and E-3-(4-chlorophenyl)propenoic acid; the compound was purified by chromatography on silica gel using ammoniated methanol/chloroform mixtures as the eluent; MS (ES$^+$) 291, 293 (MH$^+$).

Example 43

(R)-N-(1-Azabicyclo[2.2.2]oct-3-yl)-[E-3-(3,4-dichlorophenyl)propenamide]

Prepared as a free base by a method analogous to that described in Example 1 from (R)-1-azabicyclo[2.2.2]oct-3-ylamine dihydrochloride and E-3-(3,4-dichlorophenyl)propenoic acid; the compound was purified by chromatography on silica gel using ammoniated methanol/chloroform mixtures as the eluent; MS (ES$^+$) 325, 327, 329 (MH$^+$).

Example 44

(R)-N-(1-Azabicyclo[2.2.2]oct-3-yl)[E-3-(3-bromophenyl)propenamide]

Prepared as a free base by a method analogous to that described in Example 1 from (R)-1-azabicyclo[2.2.2]oct-3-

Example 45

(R)-N-(1-Azabicyclo[2.2.2]oct-3-yl)[E-3-(4-bromophenyl)propenamide]

Prepared as a free base by a method analogous to that described in Example 1 from (R)-1-azabicyclo[2.2.2]oct-3-ylamine dihydrochloride and E-3-(4-bromophenyl)propenoic acid; the compound was purified by chromatography on silica gel using ammoniated methanol/chloroform mixtures as the eluent; MS (ES$^+$) 335, 337 (MH$^+$H).

Example 46

(RS)-N-(1-Azabicyclo[2.2.2]oct-3-yl)[E-3-(3-iodophenyl)provenamide]

Prepared as a free base by a method analogous to that described in Example 1 from racemic 1-azabicyclo[2.2.2]oct-3-ylamine dihydrochloride and E-3-(3-iodophenyl)propenoic acid; MS (ES$^+$) 357 (MH$^+$).

Example 47

(RS)-N-(1-Azabicyclo[2.2.2]oct-3-yl)[E-3-(4-iodophenyl)propenamide]

Prepared as a free base by a method analogous to that described in Example 1 from racemic 1-azabicyclo[2.2.2]oct-3-ylamine dihydrochloride and E-3-(4-iodophenyl)propenoic acid; MS (ES$^+$) 357 (MH$^+$).

Example 48

(RS)-N-(1-Azabicyclo[2.2.2]oct-3-yl)[E-3-(2-trifluoromethylphenyl)propenamide]

Prepared as a free base by a method analogous to that described in Example 1 from racemic 1-azabicyclo[2.2.2]oct-3-ylamine dihydrochloride and E-3-(2-trifluoromethylphenyl)propenoic acid; MS (ES$^+$) 325 (MH$^+$).

Example 49

(R)-N-(1-Azabicyclo[2.2.2]oct-3-yl)-[E-3-(3-trifluoromethylphenyl)propenamide]

Prepared as a free base by a method analogous to that described in Example 1 from (R)-1-azabicyclo[2.2.2]oct-3-ylamine dihydrochloride and E-3-(3-trifluoromethylphenyl)propenoic acid; the compound was purified by chromatography on silica gel using ammoniated methanol/chloroform mixtures as the eluent; MS (ES$^+$) 271 (MH$^+$).

Example 50

(R)-N-(1-Azabicyclo[2.2.2]oct-3-yl)[E-3-(2-furyl)propenamide]

Prepared as a free base by a method analogous to that described in Example 1 from (R)-1-azabicyclo[2.2.2]oct-3-ylamine dihydrochloride and E-3-(2-furyl)propenoic acid; the compound was purified by chromatography on silica gel using ammoniated methanol/chloroform mixtures as the eluent; MS (ES$^+$) 247 (MH$^+$).

Example 51

(R)-N-(1-Azabicyclo[2.2.2]oct-3-yl)[E-3-(3-furyl)propenamide]

Prepared as a free base by a method analogous to that described in Example 1 from (R)-1-azabicyclo[2.2.2]oct-3-ylamine dihydrochloride and E-3-(3-furyl)propenoicacid; the compound was purified by chromatography on silica gel using ammoniated methanol/chloroform mixtures as the eluent; MS (ES$^+$) 247 (MH$^+$).

Example 52

(R)-N-(1-Azabicyclo[2.2.2]oct-3-yl)[E-3-(2-pyridyl)propenamide]

Prepared as a free base by a method analogous to that described in Example 1 from (R)-1-azabicyclo[2.2.2]oct-3-ylamine dihydrochloride and E-3-(2-pyridyl)propenoic acid; the compound was purified by chromatography on silica gel using ammoniated methanol/chloroform mixtures as the eluent; MS (ES$^+$) 258 (MH$^+$).

Example 53

(R)-N-(1-Azabicyclo[2.2.2]oct-3-yl)[E-3-(3-pyridyl)propenamide]

Prepared as a free base by a method analogous to that described in Example 1 from (R)-1-azabicyclo[2.2.2]oct-3-ylamine dihydrochloride and E-3-(3-pyridyl)propenoic acid; the compound was purified by chromatography on silica gel using ammoniated methanol/chloroform mixtures as the eluent; MS (ES$^+$) 258 (MH$^+$).

Example 54

(R)-N-(1-Azabicyclo[2.2.2]oct-3-yl)[E-3-(4-pyridyl)propenamide]

Prepared by a method analogous to that described in Example 1 from (R)-1-azabicyclo[2.2.2]oct-3-ylamine dihydrochloride and E-3-(3-pyridyl)propenoic acid. The compound was purified by chromatography on silica gel using ammoniated methanol/chloroform mixtures as the eluent. The product was dissolved in methanol, excess hydrogen chloride (1M in ether) was added. The solution was then evaporated, and recrystallisation from methanol/t-butyl methyl ether gave the dihydrochloride salt of the title compound as a colourless solid; MS (ES$^+$) 258 (MH$^+$).

Example 55

(R)-N-(1-Azabicyclo[2.2.2]oct-3-yl)[E-3-(2-thienyl)propenamide]

Prepared as a free base by a method analogous to that described in Example 1 from (R)-1-azabicyclo[2.2.2]oct-3-ylamine dihydrochloride and E-3-(2-thienyl)propenoic acid; the compound was purified by chromatography on silica gel using ammoniated methanol/chloroform mixtures as the eluent; MS (ES$^+$) 263 (MH$^+$).

Example 56

(R)-N-(1-Azabicyclo[2.2.2]oct-3-yl)[E-3-(3-thienyl)pronenamide]

Prepared by a method analogous to that described in Example 1 from (R)-1-azabicyclo[2.2.2]oct-3-ylamine dihydrochloride and E-3-(3-thienyl)propenoic acid; the compound was purified by reverse phase HPLC on a Waters Bondapak® $C_{18}$ column using a gradient of acetonitrile and 0.1% aqueous trifluoroacetic acid as the eluent. The solvent was evaporated from the product-containing fractions, then the product was dissolved in aqueous hydrochloric acid and the solution was evaporated again to give the hydrochloride salt of the title compound as a colourless solid; MS (ES$^+$) 282 (MH$^+$).

Example 57

(R)-N-(1-Azabicyclo[2.2.2]oct-3-yl)[E-3-(5-nitro-2-furyl)propenamide]

Prepared as a free base by a method analogous to that described in Example 1 from (R)-1-azabicyclo[2.2.2]oct-3-ylamine dihydrochloride and E-3-(5-nitro-2-furyl)propenoic acid; the compound was purified by chromatography on silica gel using ammoniated methanol/chloroform mixtures as the eluent; MS (ES$^+$) 293 (MH$^+$).

Example 58

(R)-N-(1-Azabicyclo[2.2.2]oct-3-yl)[E-3-(5-methoxy-3-pyridyl)propenamide]

Prepared as a free base by a method analogous to that described in Example 1 from (R)-1-azabicyclo[2.2.2]oct-3-ylamine dihydrochloride and E-3-(5-methoxy-3-pyridyl) propenoic acid; the compound was purified by chromatography on silica gel using ammoniated methanol/chloroform mixtures as the eluent; MS (ES$^+$) 288 (MH$^+$).

Example 59

(R)-N-(1-Azabicyclo]2.2.2]oct-3-yl)[E-3-(5-hydroxy-3-pyridyl)propenamide]

Prepared as a free base by a method analogous to that described in Example 1 from (R)-1-azabicyclo[2.2.2]oct-3-ylamine dihydrochioride and E-3-(5-hydroxy-3-pyridyl) propenoic acid; the compound was purified by chromatography on silica gel using ammoniated methanol/chloroform mixtures as the eluent; MS (ES$^+$) 274 (MH$^+$).

Example 60

(R)-N-(1-Azabicyclo[2.2.2]oct-3-yl)[E-3-(4-imidazolyl)propenamide]

Prepared as a free base by a method analogous to that described in Example 1 from (R)-1-azabicyclo[2.2.2]oct-3-ylamine dihydrochloride and E-3-(4-imidazolyl)propenoic acid; the compound was purified by chromatography on silica gel using ammoniated methanol/chloroform mixtures as the eluent; MS (ES$^+$) 247 (MH$^+$).

Example 61

N-(endo-8-Aza-8-methylbicyclo[3.2.1]oct-3-yl)(E-3-phenylpronenamide)

A mixture of 3α-aminotropane dihydrochloride (3.6 g), E-phenylpropenoic acid (2.5 g), 1-[3-(dimethylamino) propyl]-3-ethyl-carbodiimide hydrochloride(3.2 g), and triethylamine (12 mL) in N,N-dimethylformamide (30 mL) was stirred at room temperature overnight. The solution was evaporated, and the residue was partitioned between aqueous sodium hydroxide and chloroform. The solution was evaporated and the residue was purified by reverse phase HPLC on a Waters Bondapak® $C_{18}$ column using a gradient of acetonitrile and 0.1% aqueous trifluoroacetic acid as the eluent. The hydrochloride salt was prepared by evaporation of the product-containing fractions, dissolution of the residue in methanol, addition of excess hydrogen chloride solution (1M in diethyl ether) and evaporation. After drying under vacuum, the dihydrochloride salt of the title compound was obtained as a colourless solid (236 mg); MS (ES$^+$) 307 (MH$^+$).

Example 62

N-(exo-8-Aza-8-methylbicyclo[3.2.1]oct-3-yl)(E-3-phenylpropenamide)

A mixture of 3β-aminotropane dihydrochloride (1.83 g), E-3-phenylpropenoic acid (1.57 mg), 1-hydroxybenzotriazole hydrate (1.16 g), O-benzotriazol-1-yl-N,N,N',N'-tetramethyluronium tetrafluoroborate (2.76 g), and N,N-diisopropylethylamine (6.0 mL) in N,N-dimethylformamide (15 mL) was stirred at room temperature overnight. The solution was evaporated, and the residue was partitioned between aqueous sodium hydroxide and chloroform. The solution was evaporated and the residue was purified by reverse phase HPLC on a Waters Bondapak® $C_{18}$ column using a gradient of acetonitrile and 0.1% aqueous trifluoroacetic acid as the eluent. The hydrochloride salt was prepared by evaporation of the productcontaining fractions, dissolution of the residue in methanol, addition of excess hydrogen chloride solution (1M in diethyl ether) and evaporation. After drying under vacuum, the dihydrochloride salt of the title compound was obtained as a colorless solid (243 mg); MS (ES$^+$) 307 (MH$^+$).

Example 63

(S)-N-(1-Azabicyclo[2.2.2]oct-3-yl)[E-3-(2-furyl) propenamide]

Prepared as a free base by a method analogous to that described in Example 1 from (S)-1-azabicyclo[2.2.2]oct-3-ylamine dihydrochloride and E-3-(2-furyl)propenoic acid; the compound was purified by chromatography on silica gel using ammoniated methanol/chloroform mixtures as the eluent, followed by recrystallization from ethyl acetate/ hexane; MS (ES$^+$) 247 (MH$^+$).

What is claimed is:
1. A compound of formula I,

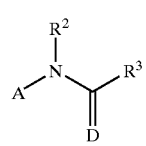

I wherein A represents:

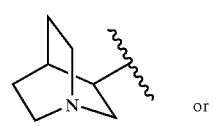

II or

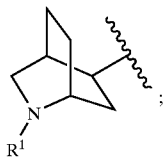

D represents oxygen, or sulfur;
R¹ represents hydrogen or methyl;
R² represents hydrogen, or $C_1$–$C_4$alkyl;
R³ represents:

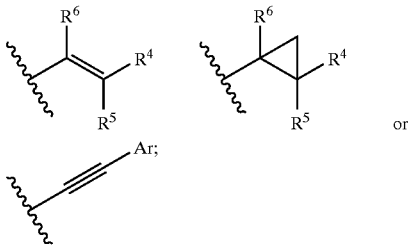

R⁴, R⁵, and R⁶ are independently at each occurrence selected from hydrogen, halogen, $C_1$–$C_4$alkyl, $C_2$–$C_4$alkenyl, $C_2$–$C_4$alkynyl, —$CO_2R^7$, —CN, —$CF_3$, or Ar, provided that at least one of R⁴ and R⁵ is Ar;

Ar represents thienyl, furyl, pyridyl or imidazolyl which may optionally be substituted with one or more substituents selected from: hydrogen, halogen, $C_1$–$C_4$alkyl, $C_2$–$C_4$alkenyl, $C_2$–$C_4$alkynyl, aryl, heteroaryl, —$CO_2R^7$, —CN, —$NO_2$, —$NR^8R^9$, —$CF_3$ or —$OR^{10}$;

R⁸, R⁹, and R¹⁰ are independently at each occurrence selected from hydrogen, $C_1$–$C_4$alkyl, aryl, heteroaryl, —$C(O)R^{11}$, —$C(O)NHR^{12}$, —$C(O)R^{13}$ or —$SO_2R^{14}$, or R⁸ and R⁹ may together be $(CH_2)_j Q(CH_2)_k$ where Q is O, S, $NR^{15}$, or a bond;

j is 2 to 4;
K is 0 to 2;

R⁷, R¹⁰, R¹¹, R¹², R¹³, and R¹⁵, are independently at each occurrence selected from $C_1$–$C_4$alkyl, aryl, or heteroaryl;

or an enantiomer thereof, or a pharmaceutically-acceptable salt thereof;

with the proviso that Ar does not represent 2-, 3-, 4-pyridyl, substituted with one or more substituents selected from $C_1$–$C_4$alkyl, $C_1$–$C_4$alkoxy, halogen, phenoxy, hydroxy, $OCOR^{11}$, $NH_2$, $NHCOR^{11}$ or nitro, when A represents:

II

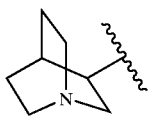

R³ represents:

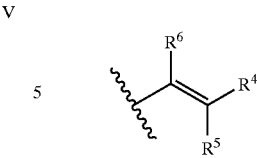

D represents oxygen;
R represents methyl;
R² and R⁵ both represent hydrogen and
R⁶ represents any of hydrogen, $C_1$–$C_4$alkyl, phenyl, or cyano.

2. A compound according to claim 1, wherein A represents:

II

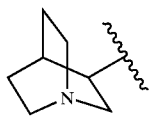

or an enantiomer thereof, or a pharmaceutically-acceptable salt thereof.

3. A compound according to claim 2, wherein R⁶ represents any of 2-furyl; 3-furyl; 2-thienyl; 3-thienyl; or an enantiomer thereof, or a pharmaceutically-acceptable salt thereof.

4. A compound according to claim 1, said compound being:
N-(1-azabicyclo[2.2.2]oct-3-yl)[E-3-(2-furyl)propenamide];
N-(1-azabicyclo[2.2.2]oct-3-yl)[E-3-(3-furyl)propenamide];
N-(1-azabicyclo[2.2.2]oct-3-yl)[E-3-(2-thienyl)propenamide];
N-(1-azabicyclo[2.2.2]oct-3-yl)[E-3-(3-thienyl)propenamide];
N-(1-azabicyclo[2.2.2]oct-3-yl)[E-3-(5-nitro-2-furyl)propenamide];
N-(1-azabicyclo[2.2.2]oct-3-yl)[E-3-(5-methoxy-3-pyridyl)propenamide];
N-(1-azabicyclo[2.2.2]oct-3-yl)[E-3-(5-hydroxy-3-pyridyl)propenamide], or
N-(1-azabicyclo[2.2.2]oct-3-yl)[E-3-(4-imidazolyl)propenamide];
or an enantiomer thereof, or a pharmaceutically-acceptable salt thereof.

5. A compound according to claim 1, said compound being:
(R)-N-(1-azabicyclo[2.2.2]oct-3-yl)[E-3-(2-furyl)propenamide];
(R)-N-(1-azabicyclo[2.2.2]oct-3-yl)[E-3-(3-furyl)propenamide];
(R)-N-(1-azabicyclo[2.2.2]oct-3-yl)[E-3-(2-thienyl)propenamide];
(R)-N-(1-azabieyelo[2.2.2]oct-3-yl)[E-3-(3-thienyl)propenamide];
(R)-N-(1-azabicyclo[2.2.2]oct-3-yl)[E-3-(5-methoxy-3-pyridyl)propenamide];
(R)-N-(1-azabicyclo[2.2.2]oct-3-yl)[E-3-(5-hydroxy-3-pyridyl)propenamide], or
(R)-N-(1-azabicyclo[2.2.2]oct-3-yl)[E-3-(4-imidazolyl)propenamide];

or an enantiomer thereof, or a pharmaceutically-acceptable salt thereof.

6. A pharmaceutical composition comprising a compound of the general formula I

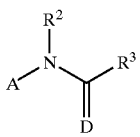

wherein A represents:

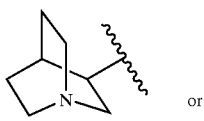 or

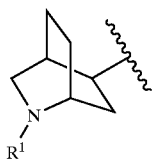

D represents oxygen, or sulfur;
$R^1$ represents hydrogen or methyl;
$R^2$ represents hydrogen, or $C_1$–$C_4$alkyl;
$R^3$ represents:

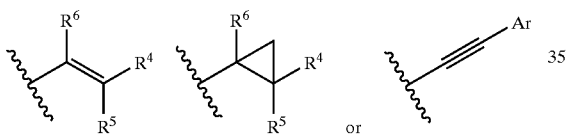

$R^4$, $R^5$, and $R^6$ are independently at each occurrence selected from hydrogen, halogen, $C_1$–$C_4$alkyl, $C_2$–$C_4$alkenyl, $C_2$–$C_4$alkynyl, —$CO_2R^7$, —CN, —$CF_3$, or Ar, provided that at least one of $R^4$ and $R^5$ represents Ar;

Ar represents thienyl, furyl, pyridyl or imidazolyl which may optionally be substituted with one or more substituents selected from: hydrogen, halogen, $C_1$–$C_4$alkyl, $C_2$–$C_4$alkenyl, $C_2$–$C_4$alkynyl, aryl, heteroaryl, —$CO_2R^7$, —CN, —$NO_2$, —$NR^8R^9$, —$CF_3$ or —$OR^{10}$;

$R^8$, $R^9$, and $R^{10}$ are independently at each occurrence selected from hydrogen, $C_1$–$C_4$alkyl, aryl, heteroaryl, —$C(O)R^{11}$, —$C(O)NHR^{12}$, —$C(O)R^{13}$ or —$SO_2R^{14}$, or $R^8$ and $R^9$ may together be $(CH_2)_j$ $Q(CH_2)_k$ where Q is O, S, $NR^{15}$, or a bond;

j is 2 to 4;
k is 0 to 2;
$R^7$, $R^{10}$, $R^{11}$, $R^{12}$, $R^{13}$, $R^{14}$, and $R^{15}$, are independently at each occurrence selected from $C_1$–$C_4$alkyl, aryl, or heteroaryl;

or an enantiomer thereof, or a pharmaceutically-acceptable salt thereof, together with a pharmaceutically-acceptable diluent or carrier.

7. A method comprising the use of a therapeutically-effective amount of a pharmaceutical composition according to claim 6, for the treatment of Alzheimer's disease, learning deficit, cognition deficit, attention deficit, memory loss, Attention Deficit Hyperactivity Disorder, anxiety, schizophrenia, or mania or manic depression, Lewy Body Dementia, Parkinson's disease, Huntington's disease, Tourette's syndrome, neurodegenerative disorders in which there is loss of cholinergic synapse, jetlag, cessation of smoking or nicotine addiction from exposure to products containing nicotine.

8. A method for the treatment of psychotic disorders or intellectual impairment disorders selected from Alzheimer's disease, learning deficit, cognition deficit, attention deficit, memory loss, Attention Deficit Hyperactivity Disorder, anxiety, schizophrenia, mania or manic depression, Lewy Body Dementia, Parkinson's disease, Huntington's disease, Tourette's syndrome, neurodegenerative disorders in which there is loss of cholinergic synapses, jetlag, cessation of smoking or nicotine addiction from exposure to products containing nicotine, comprising the administration to a subject suffering therefrom of a therapeutically effective amount of a compound of the general formula I

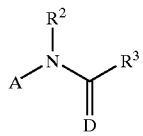

wherein A represents:

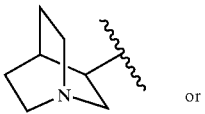 or

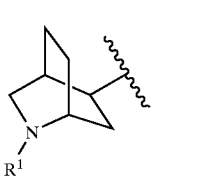

D represents oxygen, or sulfur;
$R^1$ represents hydrogen or methyl;
$R^2$ represents hydrogen, or $C_1$–$C_4$alkyl;
$R^3$ represents:

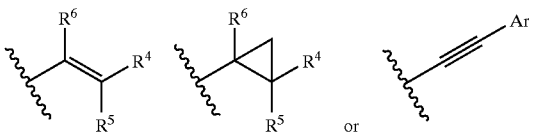

$R^4$, $R^5$, and $R^6$ are independently at each occurrence selected from hydrogen, halogen, $C_1$–$C_4$alkyl, —$C_4$alkenyl, $C_2$–$C_4$alkynyl, —$CO_2R^7$, —CN, —$CF_3$, or Ar, provided that at least one of $R^4$ and $R^5$ represents Ar;

Ar represents thienyl, furyl, pyridyl or imidazolyl which may optionally be substituted with one or more substituents selected from: hydrogen, halogen, $C_1$–$C_4$alkyl, $C_2$–$C_4$alkenyl, $C_2$–$C_4$alkynyl, aryl, heteroaryl, —$CO_2R^7$, —CN, —$NO_2$, —$NR^8R^9$, —$CF_3$ or —$OR^{10}$;

$R^8$, $R^9$, and $R^{10}$ are independently at each occurrence selected from hydrogen, $C_1$–$C_4$alkyl, aryl, heteroaryl, —C(O)R$^{11}$, —C(O)NHR$^{12}$, —C(O)R$^{13}$ or —SO$_2$R$^{14}$, or R$^8$ and R$^9$ may together be (CH$_2$)$_j$ Q(CH$_2$)$_k$ where Q is O, S, NR$^{15}$, or a bond;

j is 2 to 4;

k is 0 to 2;

R$^7$, R$^{10}$, R$^{11}$, R$^{12}$, R$^{13}$, R$^{14}$ and R$^{15}$, are independently at each occurrence selected from C$_1$–C$_4$alkyl, aryl, or heteroaryl;

or an enantiomer thereof, or a pharmaceutically-acceptable salt thereof, together with a pharmaceutically-acceptable diluent or carrier.

9. The method of claim 8, wherein said compound is:

N-(1-azabicyclo[2.2.2]oct-3-yl)[E-3-(3-furyl) propenamide];

N-(1-azabicyclo[2.2.2]oct-3-yl)[E-3-(3-furyl) propenamide];

N-(1-azabicyclo[2.2.2]oct-3-yl)[E-3-(2-pyridyl) propenamide];

N-(1-azabicyclo[2.2.2]oct-3-yl)[E-3-(3-pyridyl) propenamide];

N-(1-azabicyclo[2.2.2]oct-3-yl)[E-3-(4-pyridyl) propenamide];

N-(1-azabicyclo[2.2.2]oct-3-yl)[E-3-(2-thienyl) propenamide];

N-(1-azabicyclo[2.2.2]oct-3-yl)[E-3-(3-thienyl) propenamide];

N-(1-azabicyclo[2.2.2]oct-3-yl)[E-3-(5-nitro-2-furyl) propenamide];

N-(1-azabicyclo[2.2.2]oct-3-yl)[E-3-(5-methoxy-3-pyridyl)propenamide];

N-(1-azabicyclo[2.2.2]oct-3-yl)[E-3-(5-hydroxy-3-pyridyl)propenamide][[;]], or

N-(1-azabicyclo[2.2.2]oct-3-yl)[E-3-(4-imidazolyl) propenamide];

or an enantiomer thereof, or a pharmaceutically-acceptable salt thereof.

10. The method of claim 8, wherein said compound is:

(R)-N-(1-azabicyclo[2.2.2]oct-3-yl)[E-3-(2-furyl) propenamide];

(R)-N-(1-azabicyclo[2.2.2]oct-3-yl)[E-3-(3-furyl) propenamide];

(R)-N-(1-azabicyclo[2.2.2]oct-3-yl)[E-3-(2-pyridyl) propenamide];

(R)-N-(1-azabicyclo[2.2.2]oct-3-yl)[E-3-(3-pyridyl) propenamide];

(R)-N-(1-azabicyclo[2.2.2]oct-3-yl)[E-3-(4-pyridyl) propenamide];

(R)-N-(1-azabicyclo[2.2.2]oct-3-yl)[E-3-(2-thienyl) propenamide];

(R)-N-(1-azabicyclo[2.2.2]oct-3-yl)[E-3-(3-thienyl) propenamide];

(R)-N-(1-azabicyclo[2.2.2]oct-3-yl)[E-3-(5-nitro-2-furyl) propenamide];

(R)-N-(1-azabicyclo[2.2.2]oct-3-yl)[E-3-(5-methoxy-3-pyridyl)propenamide];

(R)-N-(1-azabicyclo[2.2.2]oct-3-yl)[E-3-(5-hydroxy-3-pyridyl)propenamide][[;]], or (R)-N-(1-azabicyclo[2.2.2]oct-3-yl)[E-3-(4-imidazolyl) propenamide];

or an enantiomer thereof, or a pharmaceutically-acceptable salt thereof.

* * * * *